United States Patent
Brown et al.

(10) Patent No.: US 9,299,738 B1
(45) Date of Patent: Mar. 29, 2016

(54) INTERPOSER BASED IMAGING SENSOR FOR HIGH-SPEED IMAGE ACQUISITION AND INSPECTION SYSTEMS

(71) Applicant: KLA-Tencor Corporation, Milpitas, CA (US)

(72) Inventors: David L. Brown, Los Gatos, CA (US); Guowu Zheng, Cupertino, CA (US); Yung-Ho Alex Chuang, Cupertino, CA (US); Venkatraman Iyer, Sunnyvale, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 14/299,749

(22) Filed: Jun. 9, 2014

Related U.S. Application Data

(63) Continuation of application No. 13/622,155, filed on Sep. 18, 2012, now Pat. No. 8,748,828.

(60) Provisional application No. 61/537,167, filed on Sep. 21, 2011.

(51) Int. Cl.
*G01T 1/20* (2006.01)
*H01L 27/146* (2006.01)
*H04N 5/335* (2011.01)

(52) U.S. Cl.
CPC ........ *H01L 27/14636* (2013.01); *H04N 5/3355* (2013.01)

(58) Field of Classification Search
CPC ................ G01N 21/9501; H01L 27/14806
USPC ............................................. 250/365
See application file for complete search history.

(56) References Cited

U.S. PATENT DOCUMENTS

| | | | |
|---|---|---|---|
| 5,525,914 A * | 6/1996 | Cao et al. | 326/71 |
| 2004/0218262 A1 * | 11/2004 | Chuang et al. | 359/366 |
| 2006/0197007 A1 | 9/2006 | Iwabuchi et al. | |
| 2008/0102552 A1 | 5/2008 | Farnworth | |
| 2010/0276572 A1 * | 11/2010 | Iwabuchi et al. | 250/208.1 |
| 2012/0306013 A1 * | 12/2012 | Donovan et al. | 257/338 |

FOREIGN PATENT DOCUMENTS

JP 2009005262 A 1/2009

* cited by examiner

*Primary Examiner* — Kiho Kim
(74) *Attorney, Agent, or Firm* — Suiter Swantz pc llo

(57) ABSTRACT

The present invention includes an interposer disposed on a surface of a substrate, a light sensing array sensor disposed on the interposer, the light sensing array sensor being back-thinned and configured for back illumination, the light sensing array sensor including columns of pixels, one or more amplification circuitry elements configured to amplify an output of the light sensing array sensor, the amplification circuits being operatively connected to the interposer, one or more analog-to-digital conversion circuitry elements configured to convert an output of the light sensing array sensor to a digital signal, the ADC circuitry elements being operatively connected to the interposer, one or more driver circuitry elements configured to drive a clock or control signal of the array sensor, the interposer configured to electrically couple at least two of the light sensing array sensor, the amplification circuits, the conversion circuits, the driver circuits, or one or more additional circuits.

19 Claims, 14 Drawing Sheets

INTERPOSER BASED IMAGING SENSOR FOR HIGH-SPEED IMAGE ACQUISITION AND INSPECTION SYSTEMS

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Patent Application entitled INTERPOSER BASED IMAGING SENSOR FOR HIGH-SPEED IMAGE ACQUISITION AND INSPECTION SYSTEMS, naming David L. Brown, Guowu Zheng, Yung-Ho Chuang and Venkatraman Iyer as inventors, filed Sep. 18, 2012, Application Ser. No. 13/622,155, which constitutes a regular (non-provisional) patent application of United States Provisional Patent Application entitled Si Interposer for High-Speed Image Acquisition and Inspection Systems Using a High-Speed Image Acquisition Sensor, naming David L. Brown, Yung-Ho Alex Chuang, Guowu Zheng, and lyer Venkatraman as inventors, filed Sep. 21, 2011, Application Ser. No. 61/537,167.

TECHNICAL FIELD

The present invention generally relates to imaging sensors suitable for implementation in semiconductor inspection systems, and more particularly, to charge coupled device based imaging sensors fabricated in a silicon interposer architecture.

BACKGROUND

As the demand for improved inspection capabilities continues to increase so too will the demand for improved image sensor devices. Typically, inspection systems utilize area sensors equipped with multiple readout registers per sensor, whereby each readout register sequentially outputs 16, 32 or more columns. A typical inspection system may use one or two sensor arrays in this regard. The image sensors included in current inspection technologies typically include charge-coupled devices (CCDs) due to their low noise and high quantum efficiency. In addition, a typical sensor array may be back-thinned and illuminated from the back, so as to maximize quantum efficiency, which is particularly advantageous at short (deep UV) wavelengths. A typical array sensor may consist of a few hundred to a few thousand pixels along each side of the sensor. Pixel dimensions are typically on the order of between about 10 µm and about 20 µm.

Typically, each image sensor is mounted on, or connected to a circuit board. The circuit board may contain drivers for driving the various clock and gate signals, amplifiers, double correlated sampling circuits and digitizers for converting the analog signals to digital signals. The circuit board may also include transmitters for transmitting the digital signals to associated image processing computers. In some cases, up to 16 digitizers may be mounted inside an assembly with an image sensor in order to help reduce the capacitance between the outputs of the sensor and the inputs of the digitizer as compared with mounting the digitizers on the circuit board. The inspection systems of the prior art, however, are limited in speed to an order of $10^9$ pixels per second, with scaling capabilities approaching $10^{10}$ pixels per second. Continued scaling beyond this level is not practical. As such, it is desirable to cure the defects of the prior art and provide methods and systems capable of extending to the speed of image sensor array based inspection technologies.

SUMMARY

An interposer-based image sensing device is disclosed. In one aspect, the device may include, but is not limited to, at least one interposer disposed on a surface of a substrate; at least one sensing array sensor disposed on the at least one interposer, the one or more light sensing array sensors being back-thinned, the one or more light sensing array sensors configured for back illumination, the one or more light sensing array sensors including a plurality of columns of pixels; at least one amplification circuitry element configured to amplify an output of the one or more light sensing array sensors, the one or more amplification circuits being operatively connected to the interposer; at least one analog-to-digital conversion circuitry element configured to convert an output of the one or more light sensing array sensors to a digital signal, the one or more analog-to-digital conversion circuits being operatively connected to the interposer; at least one driver circuitry element configured to drive at least one of a clock signal or control signal of the one or more light sensitive array sensors, the one or more driver circuitry elements being operatively connected to the interposer; and at least one additional circuitry element being operatively connected to the one or more interposers, the interposers configured to electrically couple at least two of the one or more light sensing array sensors, the one or more amplification circuits, the one or more conversion circuits, the one or more driver circuits, or the one or more additional circuits.

A method for fabricating an interposer-based image sensing device is disclosed. In one aspect, the method may include, but is not limited to, providing a substrate; disposing at least one interposer onto a surface of the substrate; and disposing a light sensitive array sensor onto a surface of the at least one interposer, the light sensitive array sensor being back-thinned and configured for back-illumination, the at least one interposer comprising at least one of one or more amplification circuitry elements configured to amplify an output of the one or more light sensing array sensors, one or more analog-to-digital conversion circuitry elements configured to convert an output of the one or more light sensing array sensors to a digital signal, one or more driver circuitry elements, or one or more additional circuitry elements.

An inspection system incorporating an interposer-based imaging device is disclosed. In one aspect, the system may include, but is not limited to, an illumination source configured to direct illumination toward a surface of a target object disposed on a sample stage; a detector, the detector comprising at least one light sensitive array device, the at least one light sensitive array device comprising at least one back-thinned light sensitive array sensor disposed on at least one interposer, the at least one back-thinned light sensitive array sensor further configured for back-illumination, the at least one interposer comprising at least one of one or more amplification circuitry elements, one or more analog-to-digital conversion circuitry elements, one or more driver circuitry elements, or one or more additional circuitry elements; a set of focusing optics configured to focus illumination onto the surface of the wafer; and a set of collection optics configured to direct illumination reflected from the surface of the target object to the detector.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 9, an imaging device 100 based upon an interposer architecture is described in accordance with the present invention.

Figure 1A:
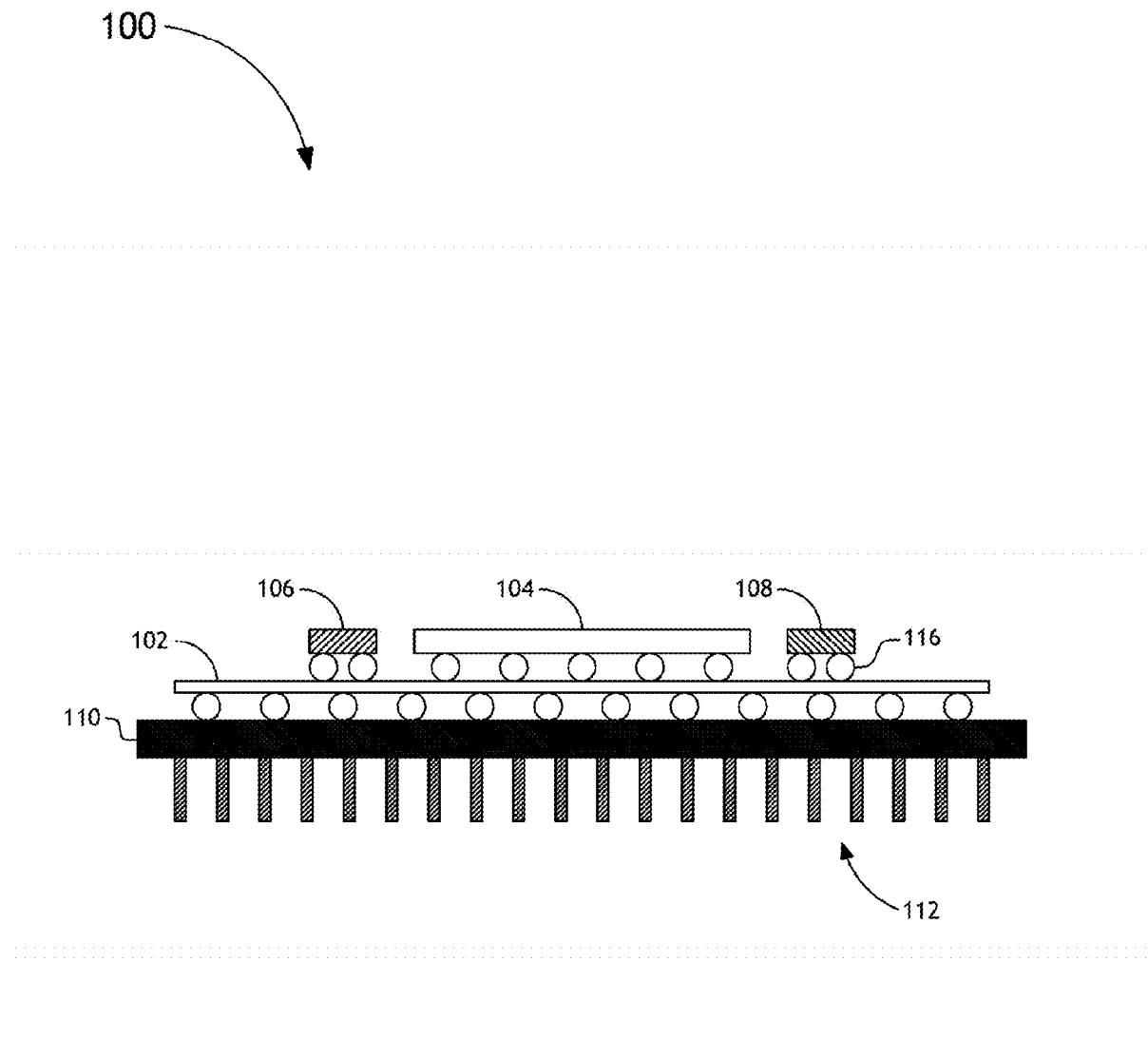
FIG. 1A illustrates a cross-sectional schematic view of an interposer-based imaging device, in accordance with an embodiment of the present invention.
Figure 1B:
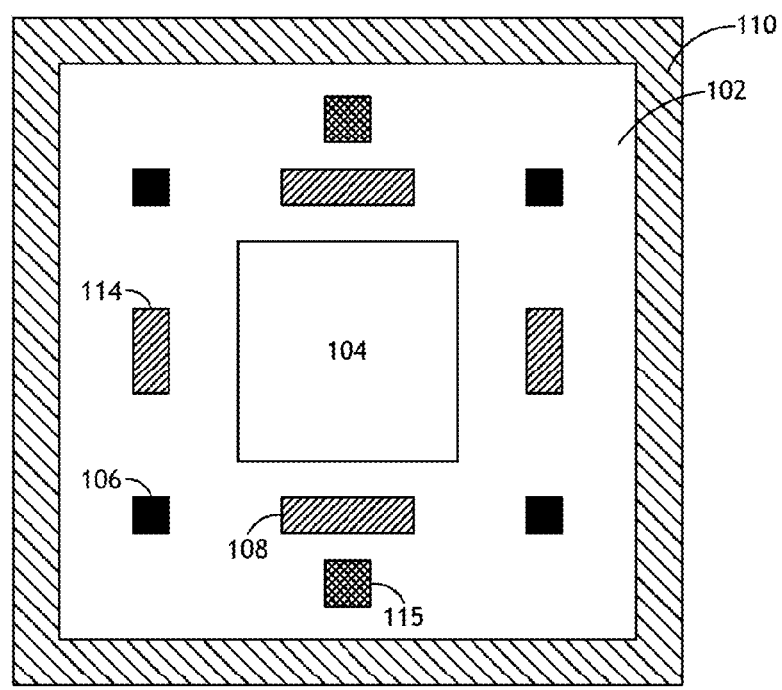
FIG. 1B illustrates a top view of an interposer-based imaging device, in accordance with an embodiment of the present invention.

FIGS. 1A and 1B illustrate simplified schematic views of an image sensing device 100 constructed utilizing an interposer 102. In one aspect of the present invention, the interposer based imaging device 100 may include one or more light sensitive sensors 104 disposed on the surface of the interposer 102. In some embodiments, as will be discussed in greater detail further herein, the one or more interposers 102 of the device 100 may include, but are not limited to, a silicon interposer. In a further aspect of the present invention, the one or more light sensitive sensors 104 of the device 100 are back-thinned and further configured for back-illumination. Those skilled in the art will recognized that a back-thinned sensor 104, when arranged in a back-illumination configuration, may increase the photon capture rate of an incident light beam, thereby increasing the overall efficiency of the image sensing device 100.

In another aspect of the present invention, various circuit elements of the image sensing device 100 may be disposed on or built into the interposer 102. In one embodiment, one or more amplification circuits (e.g., charge conversion amplifier) (not shown in FIG. 1A or 1B) may be disposed on or built into the interposer 102. In another embodiment, one or more conversion circuits 108 (e.g., analog-to-digital conversion circuits (i.e., digitizers 108)) may be disposed on or built into the interposer 102. In another embodiment, one or more driver circuits 106 may be disposed on or built into the interposer 102. For example, the one or more driver circuits 106 may include a timing/serial driver circuit. For instance, the one or more driver circuits 106 may include, but are not limited to, a clock driver circuitry element or a reset driver circuitry element. In another embodiment, one or more pixel gate driver circuit elements 114 may be disposed on or built into the interposer 102. For example, the one or more pixel gate driver circuit elements 114 may include a CCD/TDI pixel gate driver circuit element. In another embodiment, one or more optical transceivers 115 may be disposed on or built into the interposer 102. In another embodiment, one or more decoupling capacitors (not shown) may be disposed on or built into the interposer 102. In a further embodiment, one or more serial transmitters (not shown in FIG. 1A or 1B) may be disposed on or built into the interposer 102.

It is further recognized herein that various additional circuit elements may be disposed on or built directly into the interposer 102 of device 100. For example, the various circuitry elements disposed on or built into the interposer 102 may further include, but are not limited to, gate signal control circuitry, correlated double samplers, and signal conditioning circuits (e.g., filters, multiplexers, serial data output devices, buffers, digital signal processors, voltage regulators and voltage converters). By way of another example, the interposer 102 of device 100 may further include additional circuitry elements such as, but not limited to, transistors (e.g., field effect transistors, bipolar transistors, and the like), diodes, capacitors, inductors, and resistors. It is further contemplated herein that, in a general sense, any one or more circuitry elements suitable for receiving, processing, conditioning, controlling and/or transmitting signals in an imaging sensor context may be implemented within the scope of the present invention. As such, the above description related to the various circuit elements disposed on or built into the interposer 102 is not limiting, but should be interpreted as merely illustrative.

In a further embodiment, one or more of the circuit elements (e.g., driver 106 or digitizer 108) described herein may be built into the device 100 as circuits in the interposer 102. Alternatively, the one or more circuit elements described herein may comprise multiple dies that are disposed on the surface of the interposer 102.

In a further aspect of the present invention, the interposer 102 may further include logic configured to combine two or more outputs of multiple analog-to-digital converters into one or more high-speed serial bit streams for device 100 output.

In another aspect of the present invention, one or more support structures may be disposed between the bottom surface of the light sensitive array sensor 104 and the top surface of the interposer 102 in order to provide physical support to the sensor 104. In one embodiment, a plurality of solder balls 116 may be disposed between the bottom surface of the light sensitive array sensor 104 and the top surface of the interposer 102 in order to provide physical support to the sensor 104. It is recognized herein that while the imaging region of the sensor 104 might not include external electrical connections, the back-thinning of the sensor 104 causes the sensor 104 to become increasingly flexible. As such, solder balls 116 may be utilized to connect the sensor 104 to the interposer 102 in a manner that reinforces the imaging portion of the sensor 104. In an alternative embodiment, an underfill material may be disposed between the bottom surface of the light sensitive array sensor 104 and the top surface of the interposer 102 in order to provide physical support to the sensor 104. For example, an epoxy resin may be disposed between the bottom surface of the light sensitive array sensor 104 and the top surface of the interposer 102.

In another embodiment, the light sensing array sensor 104 may include an ultraviolet (UV) anti-reflection coating. In a further embodiment, the anti-reflective coating may be disposed on the back surface of the array sensor 104. In this regard, the anti-reflection coating may be grown on the back surface of the array sensor 104. In one embodiment, the UV anti-reflection coating may include a thermal oxide (e.g., silicon oxide) grown directly on a silicon surface of the array sensor 104. In another embodiment, such as in the context of an extreme UV (EUV) inspection system (see FIG. 9), an EUV anti-reflection coating may include a nitride-based material (e.g., silicon nitride). In a further embodiment, one or more additional dielectric layers may be deposited or grown on the surface of the thermal oxide layer or the nitride layer.

In another aspect of the present invention, the interposer 102 and the various additional circuit elements (e.g., amplification circuit, driver circuits 106, digitizer circuits 108, and the like) are disposed on a surface of a substrate 110. In a further aspect, the substrate 110 includes a substrate having high thermal conductivity (e.g., ceramic substrate). In this regard, the substrate 110 is configured to provide physical support to the sensor 104/interposer 102 assembly, while also providing a means for the device 100 to efficiently conduct heat away from the imaging sensor 104 and the various other circuit elements (e.g., digitizer 106, driver circuitry 108, amplifier, and the like). It is recognized herein that the substrate may include any rigid highly heat conductive substrate material known in the art. For example, the substrate 110 may include, but is not limited to, a ceramic substrate. For instance, the substrate 110 may include, but is not limited to, aluminum nitride.

In a further aspect, in settings where the device 100 includes a semiconductor-based interposer 102 (e.g., silicon-based interposer), the interposer 102 itself may include built-in active and passive circuit components such as resistors, capacitors, and transistors. Further, the driver circuitry 108 requirements may have different voltage requirements compared to the analog-to-digital conversion (ADC) circuitry elements and other readout circuitry elements. In this case, it may be advantageous to implement an interposer constructed via a manufacturing process optimized for driver circuitry, and then attach the ADC circuitry to the interposer 102 using methods known in the art, such as flip-chip or wire-bond assembly. The driver circuitry typically requires higher voltage capability, needed to generate multiple-volt swings, and may include both negative and positive voltage capability.

In another embodiment, the substrate 110 may be configured to provide an interface to a socket or an underlying printed circuit board (PCB). For example, as shown in FIG. 1A, the substrate 110 may provide interconnection between the interposer 102 and a socket or a PCB via interconnects 112. Those skilled in the art will recognize that the substrate 110 may be operatively coupled to an underlying PCB and further electrically coupled to a socket or PCB in a variety of ways, all of which are interpreted to be within the scope of the present invention.

Figure 1C:
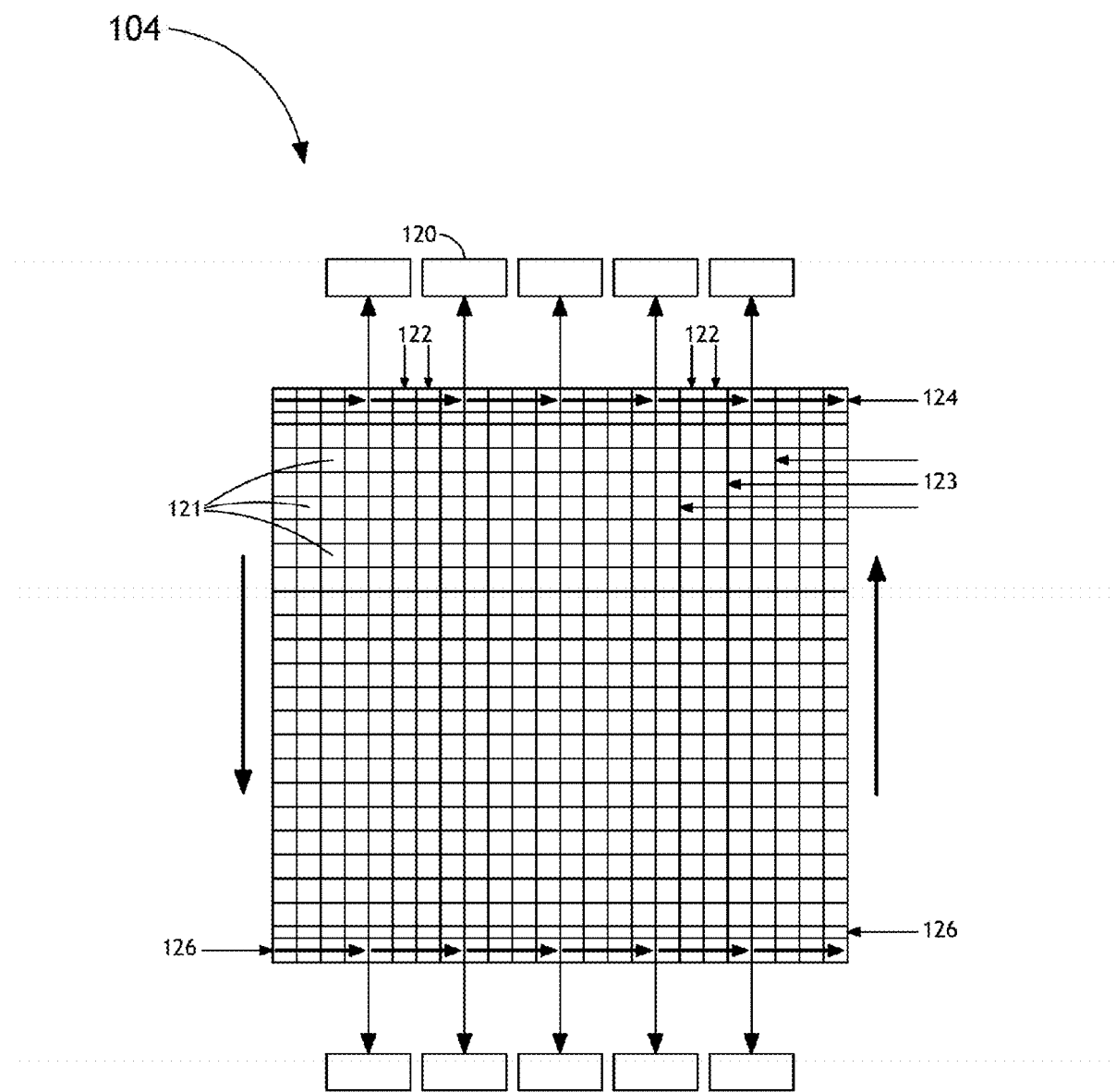
FIG. 1C illustrates a top view of a TDI array sensor, in accordance with an embodiment of the present invention.

FIG. 1C illustrates a top view of a two-dimensional light sensitive sensor suitable for use in the imaging sensor device 100, in accordance with one embodiment of the present invention. In one embodiment of the present invention, the two-dimensional light sensitive sensor array may comprise an array of charged coupled devices (CODs). In a further embodiment, the two-dimensional sensor array utilized as the array sensor 104 of device 100 of the present invention may include, but is not limited to, a time-domain integration (TDI) device. In this regard, an array of pixels, as shown in FIG. 1C, make up the imaging region 121. For instance, a TDI sensor may contain an array having a size of 256×2048 pixels or larger. Those skilled in the art will recognize that an illumination source may act to illuminate the semiconductor wafer surface (see 908 of FIG. 9). The wafer then reflects illumination onto one or more TDI sensors 104. The received photons then generate photoelectrons at the points of incidence on the sensor 104.

The TDI sensor 104 may continuously accumulate charge as it scans the wafer. The TDI sensor may in turn transfer charge along a column of pixels 122 at generally the same rate at which the sensor 104 moves with respect to the sensor image. In a further embodiment, the TDI sensor 104 may include one or more channel stops 123. The channel stops 123 prevent the movement of electrons or charge from one column to another within an imaging region 121. TDI-based array sensors are described generally in U.S. Pat. No. 7,609,309, issued on Oct. 27, 2009, which is incorporated herein by reference.

In one embodiment of the present invention, an amplifier 120 associated with an array sensor 104 is configured to receive an output of a single column of pixels of the light sensing array sensor 104. In an alternative embodiment, a single amplifier 120 associated with an array sensor 104 is configured to receive an output of two or more columns of pixels of the light sensing array sensor 104. In a further embodiment, one or more buffer amplifiers associated with a sensor 104 may be fabricated on an interposer 102 in proximity to the one or more outputs 120 of the sensor.

Figure 2:
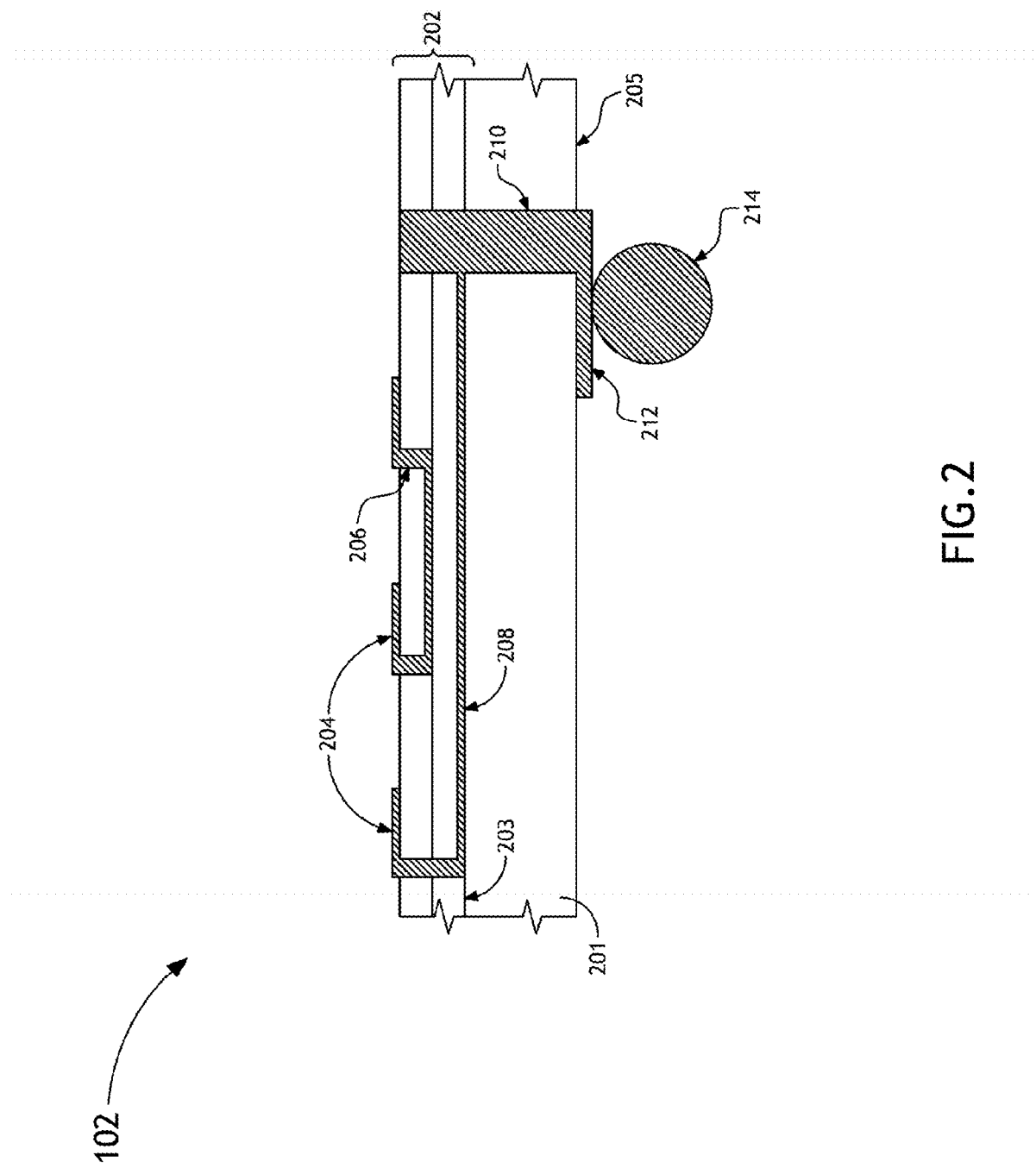
FIG. 2 illustrates a cross-sectional view of an interposer-based imaging device, in accordance with an embodiment of the present invention.

FIG. 2 illustrates a schematic cross-sectional view of a portion of the interposer 102 of the device 100. In one aspect, the interposer 102 may be disposed on a wafer 201 (e.g., silicon wafer). In a further aspect, two or more interconnect layers 202 may be formed on the top surface of the wafer 201. While the embodiment illustrated in FIG. 2 depicts two such interconnect layers, it is noted herein that any number of interconnect layers may be implemented within the context of the present invention. For instance, the interposer 102 of device 100 may include three, four, five, six, seven, or eight (and so on) interconnect layers disposed on the top surface of wafer 201. In a further aspect, one or more pads 204 may be disposed on the top surface of the one or more interconnect layers 202. It will be recognized by those skilled in the art that the pads 204 of the interposer 102 may allow for the attachment of various circuitry components and dies to the interposer 102. Such circuitry components and dies may be connected to the pads utilizing solder bumps or copper pillars (see 116 of FIG. 1A). In an additional aspect, the interposer 102 may include one or more conductive vias 206 configured to electrically couple the one or more pads 204 and other circuit components together. In some embodiments, the conductive vias 206 may include, but are not limited to, copper vias or tungsten vias. Further, the interposer 102 may include one or more conductive interconnects 208 configured to electrically couple the one or more vias 206 together. In some embodiments, the conductive interconnects 208 may include, but are not limited to, copper interconnects, aluminum interconnects, gold interconnects, or tungsten interconnects. In a general sense, it is recognized herein that the conductive vias 206 and the conductive interconnects 208 of the interposer 102 may be fabricated utilizing any conductive material known in the art to be suitable for implementation in the context of image sensing circuitry components.

In a further aspect, the interposer 102 may include one or more through-wafer vias 210 (i.e., through-silicon vias) configured to electrically couple the one or more circuit elements disposed on the top surface 203 of the wafer 201 to pads 212 disposed on the bottom surface 205 of the wafer 201. In some embodiments, the wafer 201 of the interposer 102 may be thinned to between approximately 100 µm and 200 µm in thickness before circuitry elements are disposed on the bottom 205 of the wafer 201. In a further embodiment, solder balls 214 may be attached to the pads 212, thereby allowing the interposer 102 to be attached and electrically connected to the substrate 110 (see FIGS. 1A and 1B) of the device 100.

It is contemplated herein that the interposer based architecture of the present invention allows for the sensor 104 and the associated circuitry elements (drivers, amplifiers, signal processing and digitizing circuits) to be fabricated utilizing different fabrication technologies, but disposed in close proximately to one another, thereby producing higher interconnect densities relative to conventional substrates.

Further, the high thermal conductivity of silicon allows for the efficient transfer of heat from the electronics of the devices to an associated substrate or additional heat sink.

Figure 3:
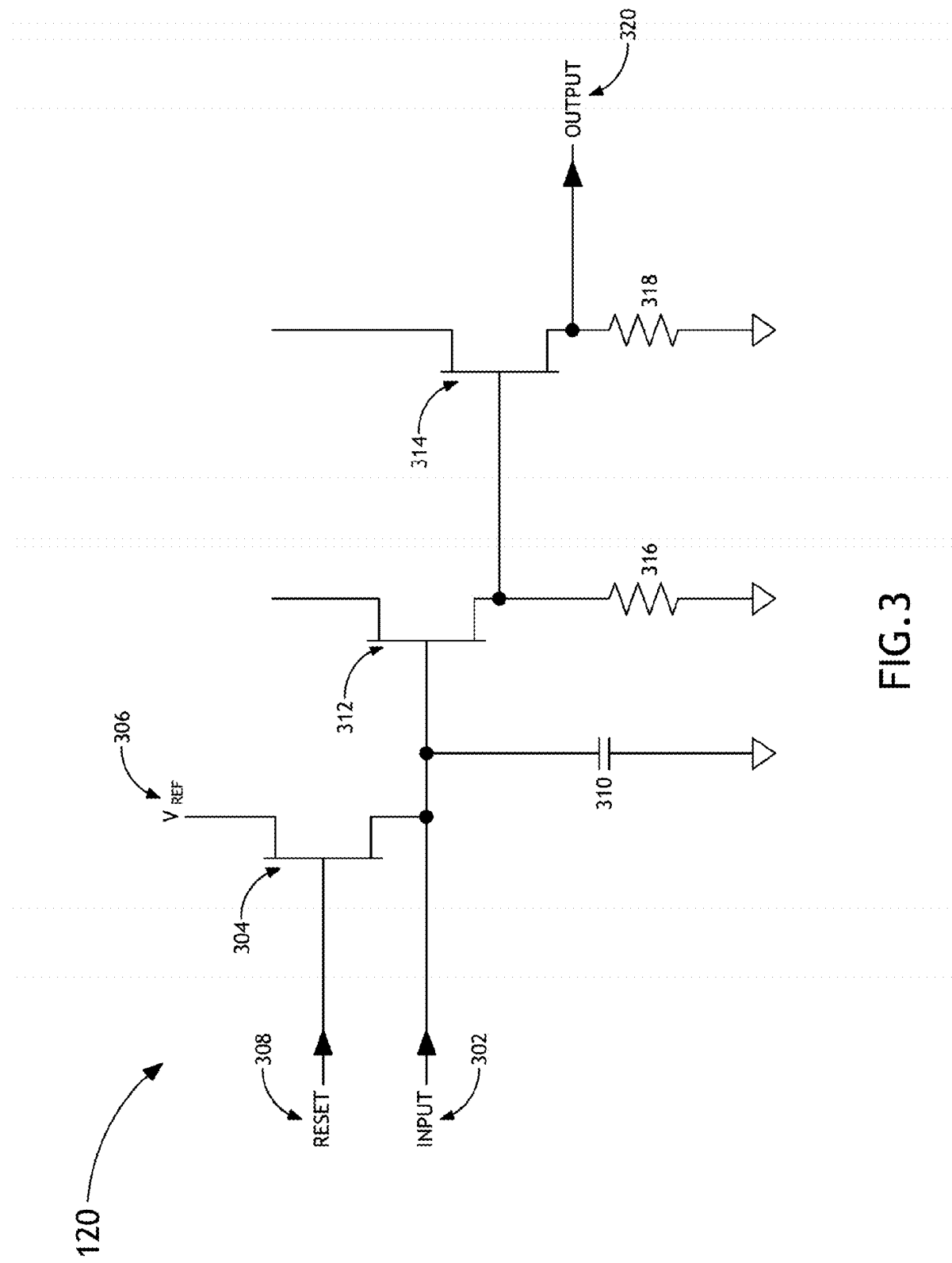
FIG. 3 illustrates a charge-conversion amplifier of an interposer-based light sensitive array sensor, in accordance with an embodiment of the present invention.

FIG. 3 illustrates a circuit diagram of a charge conversion amplifier 300, in accordance with an embodiment of the present invention. In some embodiments of the present invention, the device 100 may be configured such that each charge conversion amplifier 120 is associated with a single output of the light sensor array 104. In alternative embodiments, the device 100 may be configured such that each charge conversion amplifier 120 is associated with two or more (e.g., 2 or 4) outputs of the light sensor array 104, as shown in FIG. 1C of the present disclosure.

In one aspect of the present invention, the charge transferred from an output of the light sensitive array 104 of the device 100 is inputted into to the amplifier 120 at connection 302. In one instance, whereupon reset 308 is asserted, the transistor 304 may clamp the signal level to the reference voltage Vref 306. In another instance, when reset 308 is not asserted, charge from the input 302 is transferred to the sense node capacitor 310, thereby altering the capacitor's voltage. In a further aspect, transistors 304 and 312 act to buffer the voltage on the capacitor 310, consequently amplifying the output current. In another aspect, resistors 316 and 318 act to set the drain currents of the respective transistors, 312 and 314. Further, the output 320 of the amplifier 120 may be further configured for input into the next stage of the device 100. It is recognized herein that the above description of the amplifier 120 is not limiting and should be interpreted merely as illustrative. It is contemplated herein that other amplifier configurations may be suitable for implementation in the context of the present invention. For example, while FIG. 3 illustrates a two-transistor amplifier, it is noted herein that one- and three-transistor configurations of the amplifier 120 may also be suitable for implementation in the present invention.

In some embodiments, the charge conversion amplifiers 120 of the present invention may be incorporated into the light sensitive array sensor 104. In this manner, one or more buffers (not shown) may be placed in (or on) the interposer 102 immediately adjacent to each signal output from the light sensing array sensor 104. In such an embodiment, the capacitance that loads the output 320 is typically much smaller than in instances wherein a silicon interposer is not implemented, thereby allowing transistor 314 to be smaller, or omitted entirely. The smaller transistor 314 in turn allows for an increased number of output channels for the sensor 104 of the device 100.

Figure 4A:
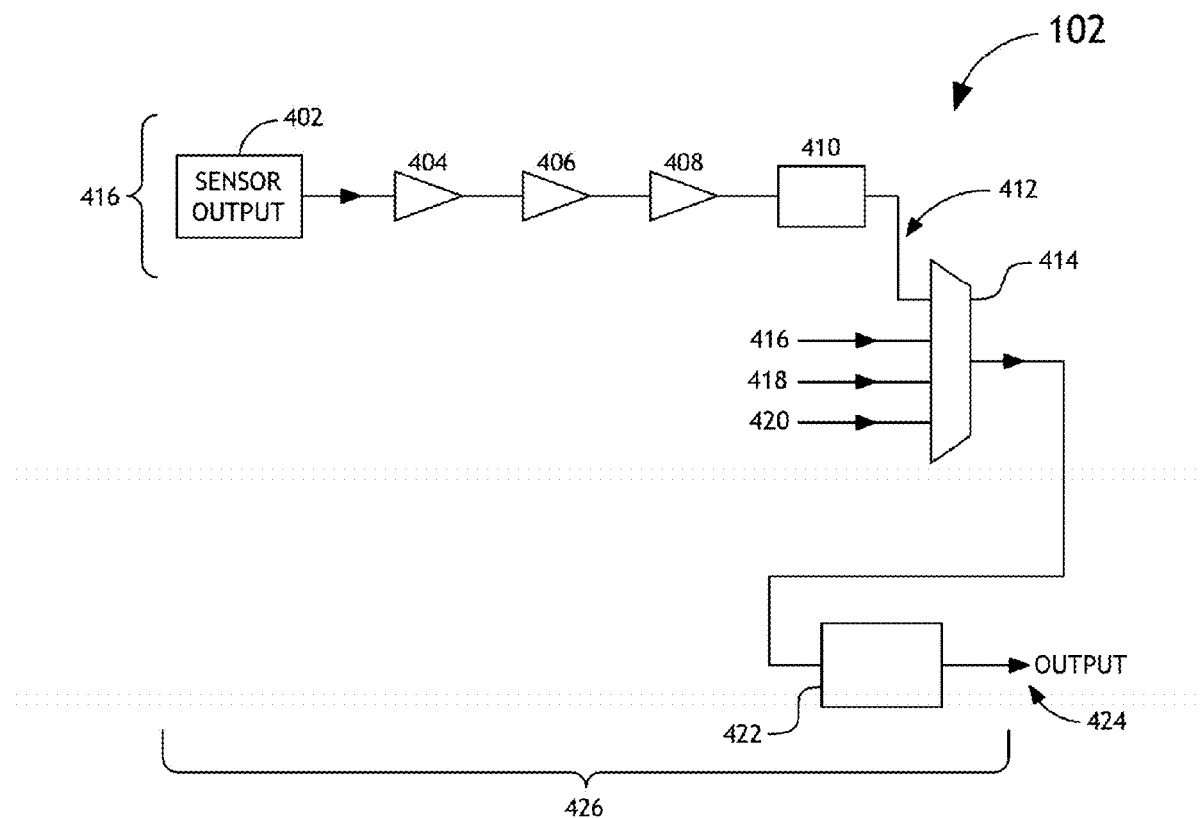
FIG. 4A illustrates a process-chain of select circuitry elements of an interposer-based imaging device, in accordance with an embodiment of the present invention.

FIG. 4A illustrates a block diagram of one arrangement of key circuit elements of the interposer-based device 100, in accordance with the present invention. In one embodiment, the circuit functions of the interposer 102 may be implemented by one or more circuit elements fabricated on the interposer 102. In another embodiment, the circuit functions of the interposer may be implemented by one or more circuit elements in multiple dies bonded on the top surface of the interposer 102. It is further recognized that the circuit functions of the interposer 102 may simultaneously be implemented via fabrication of the associated circuit elements on the interposer 102 and via multiple die bonding on the surface of the interposer 102. It is further recognized herein that, due to the relatively large area of a silicon interposer when compared to a typical integrated circuit device, yield may suffer unless the circuit density on the interposer is kept low. As such, in some embodiments, the interposer 102 may be constructed to contain a low circuit density. For example, the interposer 102 may be constructed to include interconnections and non-critical buffer circuit elements. In a further embodiment, all complex or advanced-design-rule circuit elements may be implemented in separate dies that are fabricated and tested prior to being attached to the interposer 102.

In one aspect, one or more output signals from the light sensitive array sensor 104 may be inputted into the interposer 102 circuitry at 402. In this sense, the input signal (i.e., the output signal from sensor 104) may emanate from one or more charge conversion amplifiers 120, such as those amplifiers depicted in FIG. 1C or the embodiment of amplifier 120 depicted in FIG. 3. In a first step, the signal may be transmitted to a buffer 404. It is recognized herein that minimization of capacitive load that buffer 404 places on the signal output from the light sensitive array sensor 104 is of relative importance. In some embodiments, the buffer 404 may be fabricated in the interposer 102 such that the buffer 404 is positioned in close proximity to the output connector of the sensor 104 that will feed into the buffer 404. Then, the output of the buffer 404 is coupled to a correlated double sampling module 406. Further, the output of the double correlated sampling module 406 is converted to a digital signal utilizing the analog-to-digital converter 408. Next, the output of the analog-to-digital converter 408 may be buffered via a FIFO buffer

410. The buffered digital signal from the FIFO buffer 410 may then transmitted as one input 412 into a multiplexer 414.

In a further embodiment, the processing chain 416 (i.e., the circuit elements described above) may be replicated multiple times to accommodate multiple outputs from the light sensitivity array sensor 104, with each processing chain 416 connected to a separate input of the multiplexer 414 (e.g., input 416, input 418, input 420 and so on). It is recognized herein that the multiplexer 414 depicted in FIG. 4A is not limiting and should be interpreted merely as illustrative. For instance, it is noted that the multiplexer 414 may include fewer than four inputs or more than four inputs. Further, the output from the multiplexer 414 is converted to a high-speed serial signal by serial converter and driver 422 and is then outputted from the interposer at output connector 424.

Figure 9:
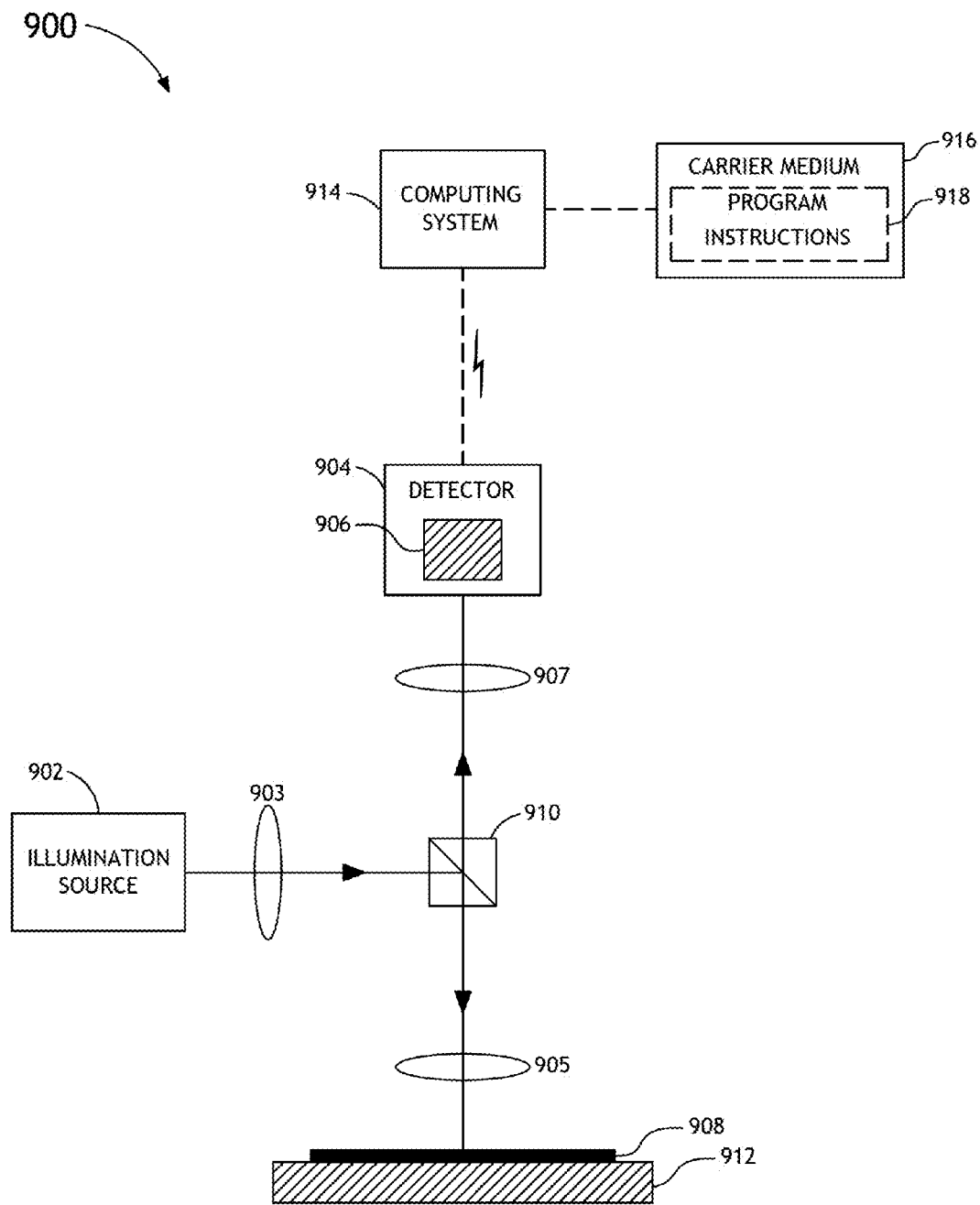
FIG. 9 illustrates an inspection system having a detector incorporating an interposer-based imaging device, in accordance with an embodiment of the present invention.

In a further embodiment, the serial output(s) 424 from the high-speed serial drivers 422 may be transmitted by one or more fiber optic cables to the image processing computer of an inspection tool (see FIG. 9). In some embodiments, the fiber optic transmitters may be mounted on the silicon interposer 102. In alternative embodiments, the fiber optic transmitters may be may mounted on the substrate 110. In additional embodiments, the fiber optic transmitters may be mounted on a printed circuit board (PCB) in proximity to the connector for the substrate 110. Due to the high speed of the serial transmission, it is necessary to minimize the capacitance between the output of the serial data driver 422 and the fiber optic transmitter(s). Installing the fiber optic transmitters on the interposer 102 or on the substrate 110 allows the fiber optic transmitters to be placed close to the serial data drivers 422 with minimized capacitance on the connecting signal(s). It is recognized herein that the reduction of capacitance aids in reducing the drive current needed to drive the one or more signals of the device 100, thereby reducing the overall power consumed by the device 100.

Figure 4B:
FIG. 4B illustrates one or more buffers and drivers of the interposer for clock signals of an interposer-based imaging device, in accordance with an embodiment of the present invention.

In another embodiment, illustrated in FIG. 4B, interposer 102 may include one or more buffers and/or drivers for clock signals. For example, clock signal 430 may be transmitted to clock driver 432 and then sent to the light sensitive image sensor 104 as signal 434. In further embodiments, there may exist multiple (e.g., two, three, four, or more) clock signals for each sensor 104, in which case multiple drivers 432 may be utilized. By way of another example, illustrated in FIG. 4C, control signal 440 may be buffered by buffer/driver 442 and then sent to the light sensitive array sensor 104 as signal 444. Again, there may exist multiple control signals, thereby requiring multiple associated buffer/drivers 442. In a further embodiment, the buffers and drivers for the clock and control signals may be implemented as circuitry devices attached to the interposer 102 or as circuits within the interposer 102. In another embodiment, the buffers and drivers for the clock and control signals may be implemented on a PCB and configured to pass signals through the interposer 102 to the light sensitive image sensor 104.

Figure 4C:
FIG. 4C illustrates one or more buffers and drivers of the interposer for control signals of an interposer-based imaging device, in accordance with an embodiment of the present invention.

It is recognized herein that the description of FIGS. 4A-4C is not limiting and should be interpreted merely as illustrative. It is further recognized herein that all of the functions shown above may be implemented in or on the interposer assembly. Further, it is contemplated that additional embodiments may include additional functions not shown in FIGS. 4A-4C. Moreover, it is further recognized that the specific sequence illustrated in FIGS. 4A-4C is not limiting as it is contemplated that the functions of FIGS. 4A-4C may be connected in a sequence different from that shown in FIGS. 4A-4C. For example, after the signal has been digitized by the analog-to-digital converter 408, there are a variety of ways in which to combine multiple digital signals into one or more high-speed serial data streams.

Figure 5:
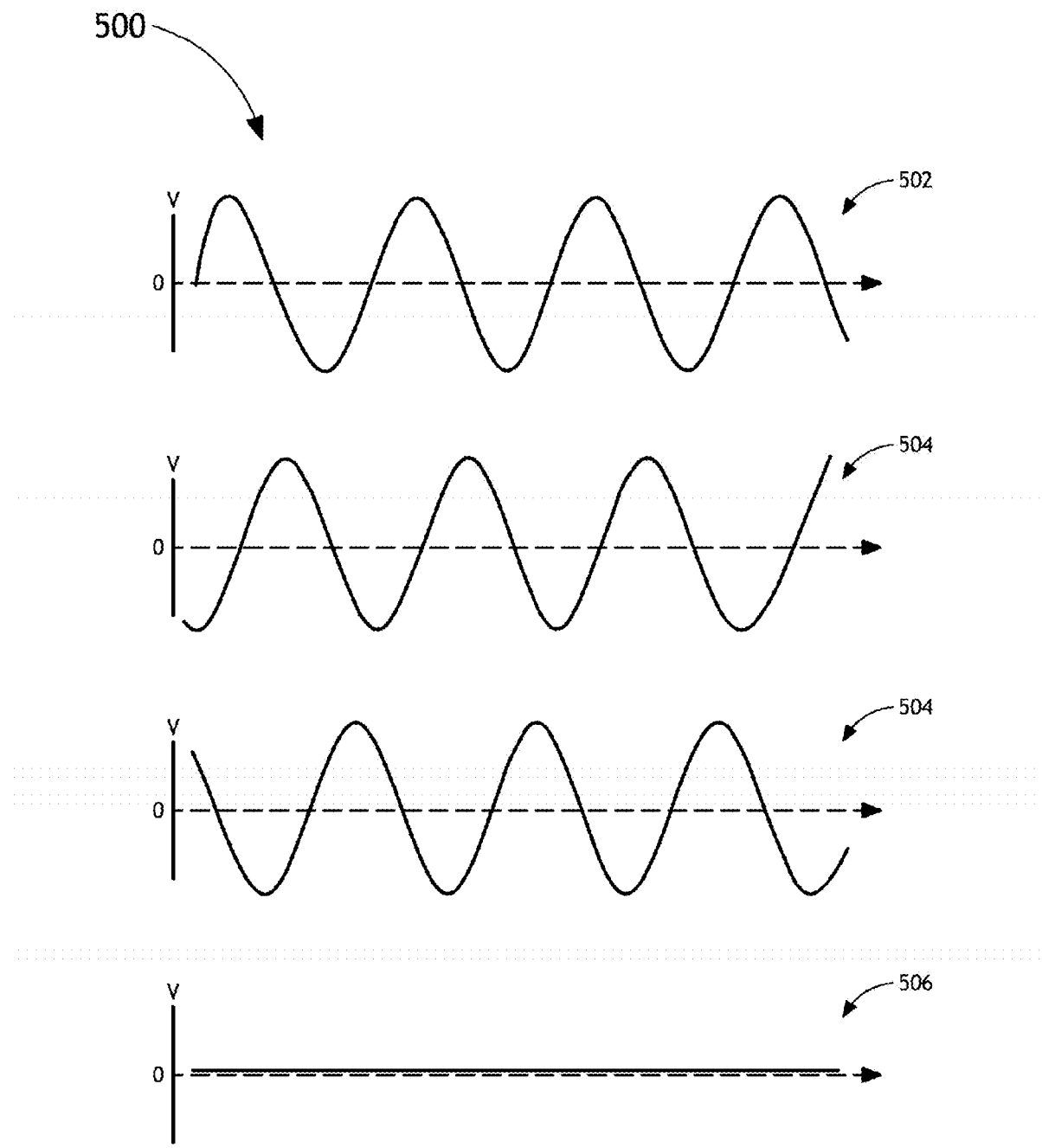
FIG. 5 illustrates a multi-phase clock signal used to drive the light sensitive array sensor of an imaging device, in accordance with an embodiment of the present invention.

FIG. 5 illustrates a multiphase clock signal that is suitable to drive the light sensitive array sensor 104 of the device 100. While FIG. 5 illustrates a three-phase clock signal, it is recognized that additional signals may be suitable for implementation in the present invention. For example, the clock signal may include, but is not limited to, a 2-phase or 4-phase clock signal, depending on the design of the light sensitive array detector 104. As shown in FIG. 5, in certain preferred embodiments, the clock signals are approximately sinusoidal in shape. In other embodiments, the clock signals utilized in the present invention may include additional waveforms, such as, but not limited to, square waveforms or trapezoidal waveforms. As such, the sine wave based clock signals illustrated in FIG. 5 are not limiting and should be interpreted merely as illustrative. Examples of clock signal waveforms suitable for implementation in the present invention are described generally in U.S. Pat. No. 7,609,309, issued on Oct. 27, 2009, which is incorporated herein by reference.

Figure 6A:
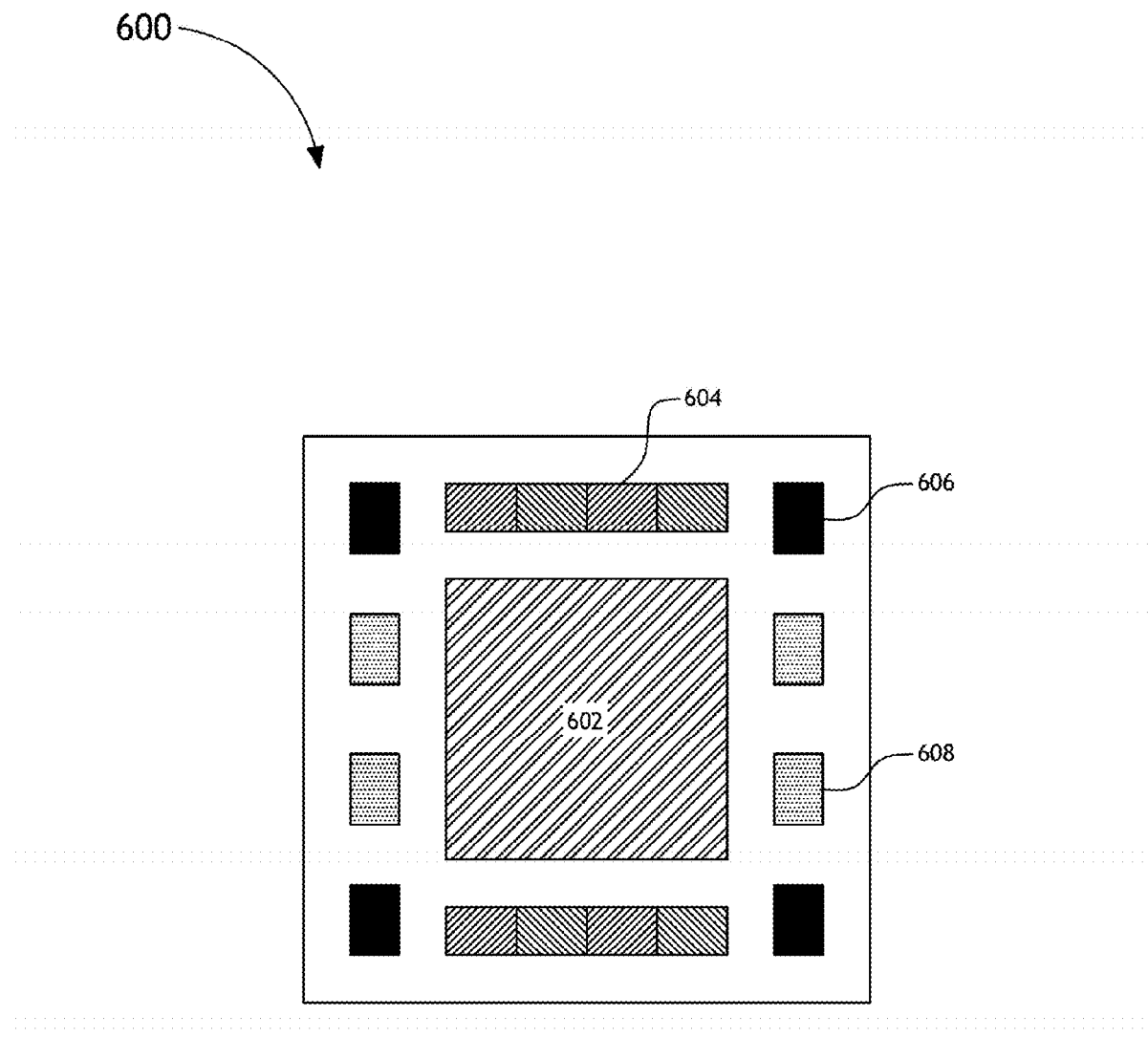
FIG. 6A illustrates a top view of a TDI sensor module, in accordance with an embodiment of the present invention.
Figure 6B:
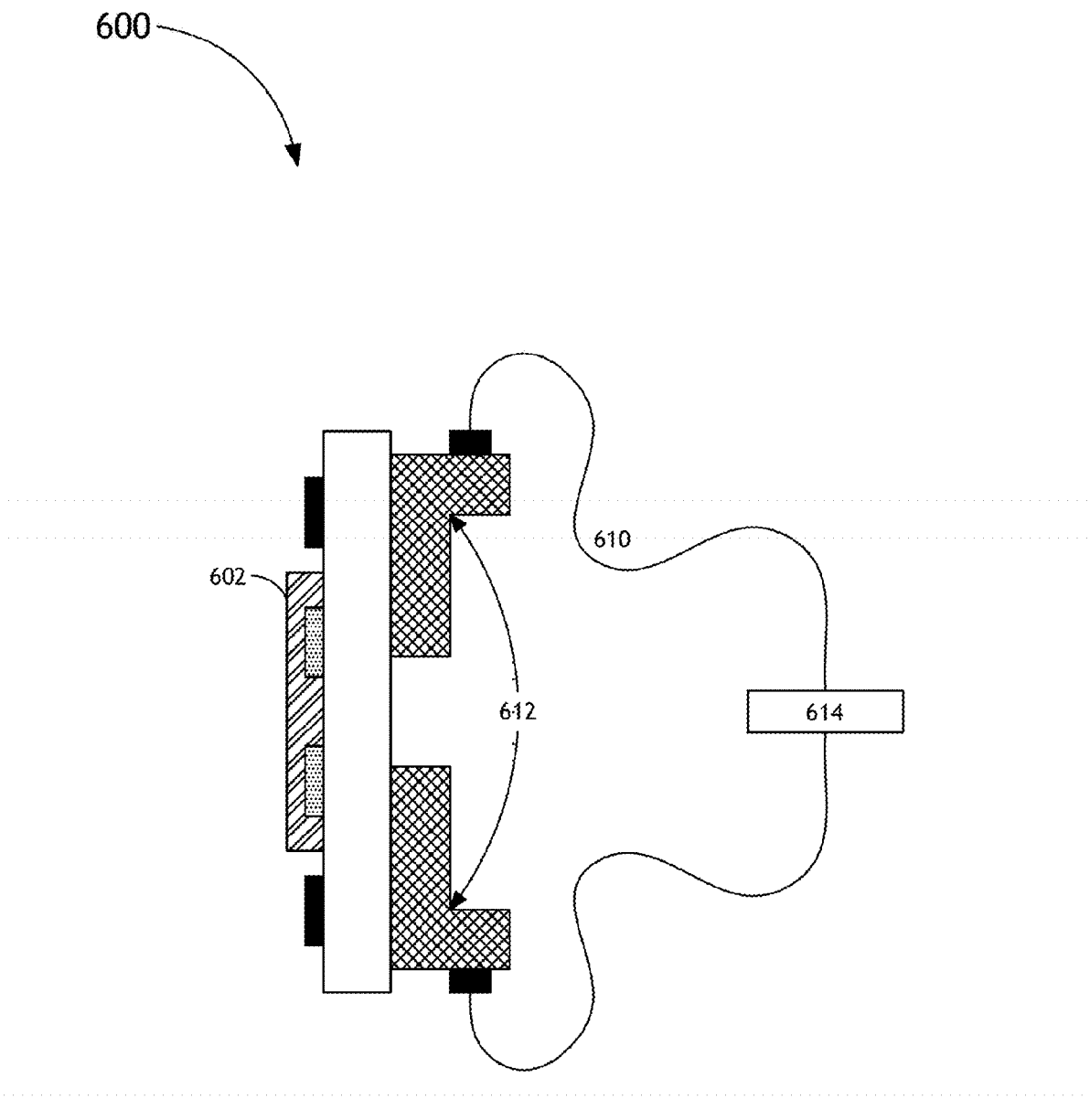
FIG. 6B illustrates a side view of a TDI sensor module, in accordance with an embodiment of the present invention.
Figure 6C:
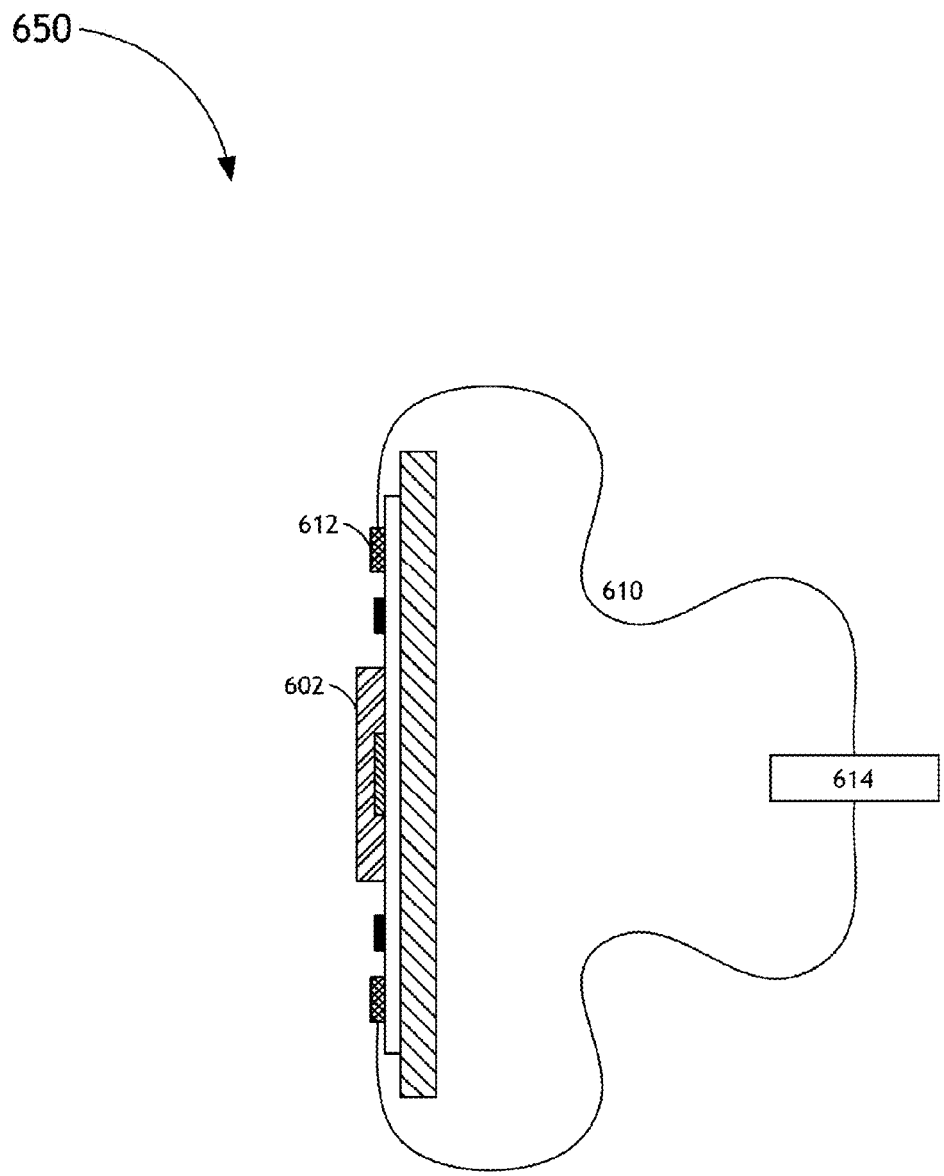
FIG. 6C illustrates a side view of a TDI sensor module, in accordance with an embodiment of the present invention.

FIGS. 6A through 8B illustrate the implementation of multiple light sensitive array sensors 104 in device 100. FIGS. 6A-6C illustrate top views and side views of a single TDI-based light sensitive sensor module 600. The TDI-based sensor module 600 may include, but is not limited to, localized driving and signal processing circuitry. For example, the sensor module 600 may include a TDI sensor 602, processing circuits 604 configured to process signals from the sensor 602, timing and serial drive circuits 606, and pixel gate driver circuits 608. As shown in FIG. 6B, the sensor module 600 may further include optical fibers 610 attached to data transceivers 612 (e.g., optical transceivers) of the module 600 in order to allow for the communication of the driving/processing data between the TDI sensor module 600 and inspection components 614 of an implementing inspection system (see FIG. 9). In an alternative embodiment, as shown in FIG. 6C, the optical fibers 610 may be attached to data transceivers 612 disposed on the same side of the interposer of the module 600 as the sensor 602.

Figure 7:
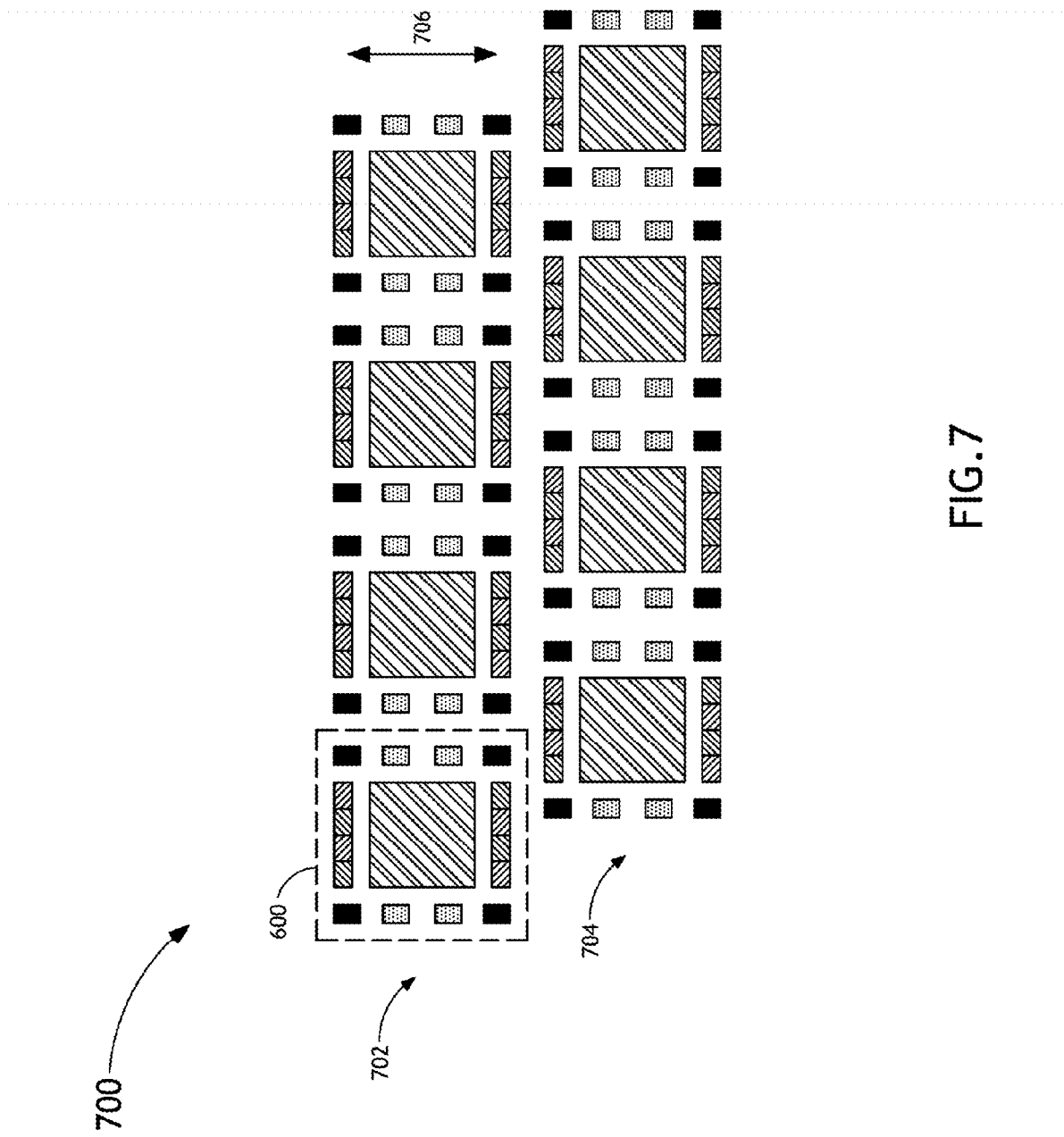
FIG. 7 illustrates a top view of a TDI sensor module array, in accordance with an embodiment of the present invention.

FIG. 7 illustrates the implementation of multiple TDI-based image sensor modules 600 into an image sensor module array 700. In one embodiment, the TDI sensors 602 of modules 600 of adjacent rows may be aligned such that approximately 100% image coverage is achieved when used in a continuous scanning configuration. For example, in the embodiment shown in FIG. 7, the upper row 702 may be offset with respect to the lower row 704 such that the TDI sensor 602 of one row is positioned in the gap produced by the driving/processing circuits of an adjacent row. Moreover, in order to ensure no gaps exist in the image coverage, the width of each TDI sensor 602 is equal to or greater than the space between TDI sensors. In this configuration, as the inspected wafer/mask/reticle is being moved in a TDI image scan direction 706, sensor module array 700 may aid in maximizing EUV wavelength image capture.

Figure 8A:
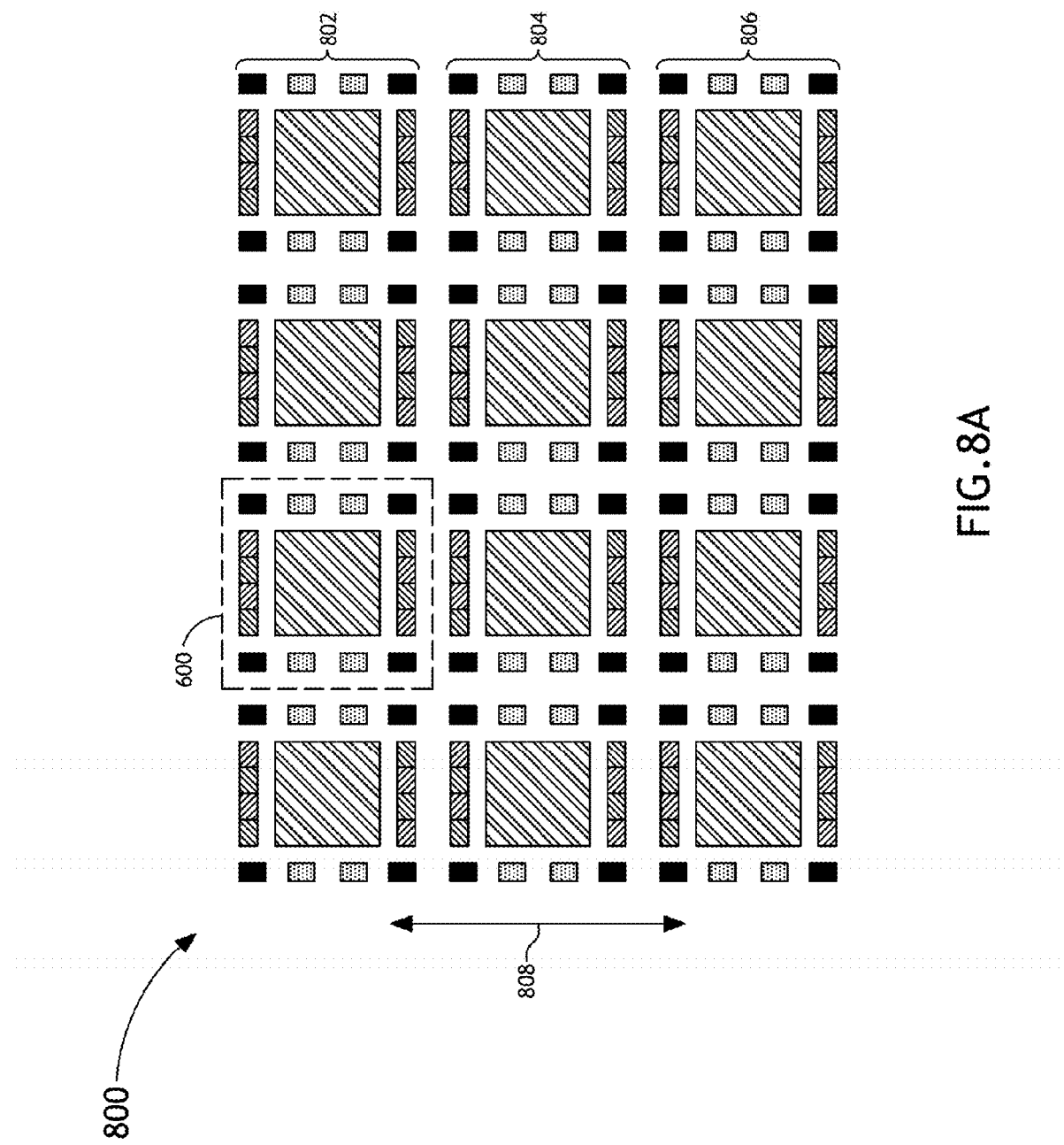
FIG. 8A illustrates a top view of a TDI sensor module array, in accordance with an embodiment of the present invention.

FIG. 8A illustrates an alternate implementation of multiple TDI-based image sensor modules 600 into an image sensor module array 800. In this embodiment, integration of the detected data may be increased through the alignment of columns of TDI sensor modules 600. For example, rows 802, 804, and 806 of sensor modules 600 may capture and process imagery data samples of the same, or similar, optical image. As such, the array 800 may provide a data stream for each swath of an inspected wafer, mask, or reticle. In this manner, integration may minimize the fluctuations associated with a plasma light source. Array 800 may also act to reduce the uniformity and stability requirements of plasma light sources needed in an implementing inspection system (see FIG. 9), thereby improving the manufacturability and operating lifetime of implementing inspection systems.

Figure 8B:
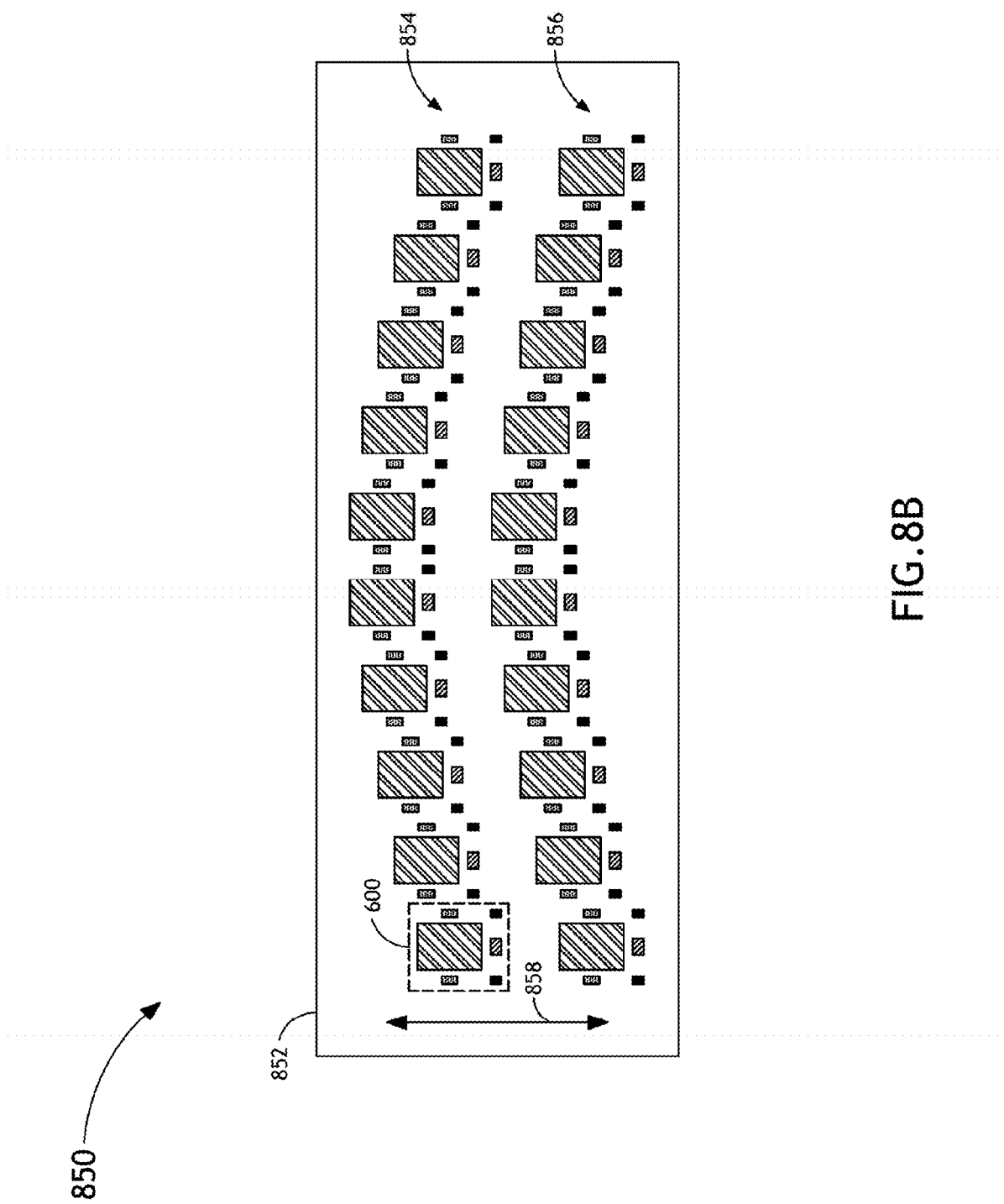
FIG. 8B illustrates a top view of a non-rectangular TDI sensor module array, in accordance with an embodiment of the present invention.

FIG. 8B illustrates an alternate implementation of multiple TDI-based image sensor modules 600 into a non-rectangular image sensor module array 850. In this embodiment, rows 854 and 856 of sensor modules 600 may be arranged in a non-rectangular grid pattern on the interposer 852, such as that illustrated in FIG. 8B. Further, the modules of rows 854 and 856 may be configured such that they output interleaved image output data streams. The non-rectangular arrangement of sensor modules 600 may improve uniformity in settings where illumination is not uniform in the field and may aid in reducing aberrations. It is anticipated that the non-rectangular image sensor module array may be utilized to detect a variety of illumination types. In particular, it is anticipated that the non-rectangular image sensor array 850 may be particularly advantageous in EUV applications.

TDI-based sensors, sensor modules, and sensor module arrays are described generally in U.S. patent application Ser. No. 12/812,950, filed on Jun. 18, 2010, which is incorporated herein by reference.

In a further embodiment, it is contemplated herein that multiple image sensors 104 (e.g., TDI sensors) might be mounted on one silicon interposer 102 or multiple interposers 102 may be mounted side by side, or both, in order to increase the light collection area. Arrays 700, 800, and 850 illustrate sensor module arrays with which the interposer-based sensors 104 of the present disclosure may be extended. It is further noted herein that the module arrays 700, 800, and 850 examples are not limiting and should merely be interpreted as illustrative. It is anticipated herein that the light sensitive array sensors 104 described throughout the present disclosure may be implemented into a variety of sensor modular array patterns.

FIG. 9 illustrates an inspection system 900 incorporating one or more of the interposer-based imaging devices 100 described throughout the present disclosure.

In one aspect, the inspection system 900 is configured to detect defects on a semiconductor wafer 908 disposed on a sample stage 912. The inspection system 900 may include any appropriate inspection system known in the art, such as, but not limited to, a bright-field inspection system or a dark-field inspection system. In a further aspect, the inspection system 900 may be configured to operate in both bright-field and dark-field mode. In another aspect, the inspection system 900 may be configured with reflecting optics to operate as an extreme UV (EUV) photomask inspection system operating at a EUV wavelength. For example, the inspection system 900 may be configured to operate at or near a wavelength of 13.5 nm or wavelength of 5 nm. In a general sense, although not illustrated, the inspection system 900 may include any inspection system suitable for inspecting one or more wafers, reticles, or photomasks.

In a further aspect, the inspection system 900 may include an illumination source 902, a detector 904 equipped with an interposer based imaging device 906, and a beam splitter 910. It is recognized herein that the interposer based imaging device 100 as described previously herein and throughout the present disclosure may be utilized as the one or more imaging devices 906 of the inspection system 900. As such, the description of the light sensitive array sensor 104 and the imaging device 100 should be interpreted to apply to the imaging device 906 of system 900. In this sense, the TDI sensor of imaging device 906 includes a two-dimensional light-sensitive array mounted on a silicon interposer. The silicon interposer may include amplifier circuits that are connected to each column output from the light sensitive array. The silicon interposer assembly may further include drivers for driving the clock and other control signals of the light-sensitive array, correlated double sampling modules and digitizers for converting the outputs of said amplifiers into a digital signal and outputting a serial bit stream. The driver and digitizer functions may be built in as circuits in the interposer, or may consist of multiple dies that are disposed on the silicon interposer, or a combination of both.

The illumination source 902 may include any illumination source known in the art. For example, the illumination source 106 may include a narrow band light source, such as a laser source. By way of another example, the illumination source 902 may include a broad band source, such as a Xenon lamp. In further embodiments, the illumination source 902 may be configured to generate EUV light. For example, the EUV light source may include a discharge produced plasma (DPP) light source or a laser produced plasma (LPP) light source configured to generate light in the EUV range. For instance, the EUV illumination source may generate light at or near a wavelength of 13.5 nm or wavelength of 5 nm.

In some embodiments, as illustrated in FIG. 9, the illumination source 902 may be configured to direct light to a beam splitter 910. In turn, the beam splitter 910 may be configured to direct light from the illumination source 902 to the surface of the wafer 908 disposed on the sample stage 912. Further, the beam splitter 910 may be configured to transmit light reflected from wafer 908 to the detector 904.

The detector 904 may include any appropriate detector known in the art. In one aspect, the detector 904 may include a charge coupled device based detector. In this regard, the detector 904 may incorporate the imaging device 100 and light sensitive array sensor 104 as described throughout the present disclosure. In other embodiments, the detector 904 may be configured to incorporate multiple array sensors arranged contiguously. For instance, detector 904 may incorporate sensor module arrays, such as sensor module array 700, 800, and 850 described previously herein.

In another embodiment, the output of the detector 904 may be communicatively coupled to the one or more computing systems 914. In this regard, the one or more computing systems 914 may be configured to detect actual defects on wafer 908 using detection data collected and transmitted by the detector 904. The one or more computing systems 914 may utilize any method and/or algorithm known in the art to detect defects on the wafer. Those skilled in the art should recognize that the inspection system 900 may be utilized to detect defects distributed across the semiconductor wafer. For example, the inspection system 900 may be configured to detect multiple defects distributed across multiple dies of the wafer 908.

Further, the one or more computing systems 914 may be coupled to the detector 904 in any suitable manner (e.g., by one or more transmission media indicated by the dotted line shown in FIG. 9, which may include any suitable transmission media known in the art) such that the computing system 914 can receive the output generated by the detector 904. Furthermore, if the inspection system 900 includes more than one detector (not shown), the one or more computing systems 914 may be coupled to each detector as described above. In a further embodiment, the wafer 908 may be disposed on a sample stage 912. The sample stage 912 may include any appropriate mechanical and/or robotic assembly known in the art.

In a further embodiment, the inspection system 900 may be configured to accept instructions from another subsystem of the system 900 in order to dynamically identify defects of the semiconductor wafer 908. For instance, the inspection system 900 may accept instructions from one or more computing systems 914 of the system 900. Upon receiving the instructions from the one or more computing systems 914, the inspection system 900 may perform an inspection process at the locations of the semiconductor wafer 908 identified in the provided instructions. The one or more computing systems 914 may be configured to perform any other step(s) of any of the embodiments described herein.

In another embodiment, the one or more computing systems 914 of the system 900 may be configured to receive and/or acquire data or information from other systems (e.g., inspection results from an additional inspection system or metrology results from a metrology system) by a transmission medium that may include wireline and/or wireless portions. In this manner, the transmission medium may serve as a data link between the one or more computing systems 914 and other subsystems of the system 900. Moreover, the one or more computing systems 914 may send data to external systems via a transmission medium.

The one or more computing systems 914 may include, but are not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 918 implementing methods such as those described herein may be transmitted over or stored on carrier medium 916. The carrier medium 916 may be a transmission medium such as a wire, cable, or wireless transmission link. The carrier medium 916 may also include a storage medium such as a read-only memory, a random access memory, a magnetic or optical disk, or a magnetic tape.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed:

1. An interposer-based image sensing device, comprising:
   at least one interposer disposed on a surface of a substrate;
   at least one light sensing array sensor disposed on the at least one interposer, the at least one light sensing array sensor being back-thinned, the at least one light sensing array sensor configured for back illumination, the at least one light sensing array sensor including a plurality of columns of pixels, the at least one interposer positioned between the substrate and the at least one light sensing array sensor;
   at least two analog-to-digital conversion circuitry elements configured to convert one or more outputs of the at least one light sensing array sensor to one or more digital signals, the at least two analog-to-digital conversion circuits being fabricated on the interposer; and
   at least one multiplexer being operatively connected to the interposer and being configured to combine the one or more digital signals from the at least two analog-to-digital conversion circuits, the interposer configured to electrically couple the at least one light sensing array sensor and the at least two analog-to-digital conversion circuits.

2. The apparatus of claim 1, wherein the at least one multiplexer is fabricated on the interposer.

3. The apparatus of claim 1, further comprising at least one driver circuitry element configured to drive at least one of a clock signal or a control signal of the at least one light sensitive array sensor, the at least one driver circuitry element being operatively connected to the interposer.

4. An interposer-based image sensing device, comprising:
   at least one interposer disposed on a surface of a substrate;
   at least one light sensing array sensor disposed on the at least one interposer, the at least one light sensing array sensor being back-thinned, the at least one light sensing array sensor configured for back illumination, the at least one light sensing array sensor including a plurality of columns of pixels, the at least one interposer positioned between the substrate and the at least one light sensing array sensor;
   at least two buffer circuits configured to accept outputs of the at least one light sensing array sensor, the at least two buffer circuits being fabricated on the interposer; and
   at least two correlated double sampling modules being operatively connected to the interposer and being configured to accept one or more outputs from the at least two buffer circuits, the interposer configured to place each buffer proximate to the output of the at least one light sensing array electrically coupled to the interposer.

5. The apparatus of claim 4, further comprising at least two analog-to-digital conversion circuitry elements configured to convert one or more outputs of the at least two double-correlated sampling modules to one or more digital signals, the at least two analog-to-digital conversion circuits being operatively connected to the interposer.

6. An inspection system, comprising:
   an illumination source configured to direct illumination toward a surface of a target object disposed on a sample stage;
   a detector, the detector comprising at least one light sensing array device, the at least one light sensing array device comprising:
   at least one back-thinned light sensing array sensor disposed on at least one interposer, the at least one back-thinned light sensing array sensor further configured for back-illumination, the at least one interposer positioned between the substrate and the at least one light sensing array sensor; and
   at least two analog-to-digital conversion circuitry elements fabricated on the at least one interposer, the at least two analog-to-digital conversion circuits configured to convert one or more outputs of the at least one light sensing array sensor to one or more digital signals, the at least one light sensing array device further comprising at least one multiplexer being operatively connected to the interposer and being configured to combine the one or more digital signals from the at least two analog-to-digital conversion circuits;
   a set of focusing optics configured to focus illumination onto the surface of the target object; and
   a set of collection optics configured to direct illumination reflected from the surface of the target object to the detector.

7. The inspection system of claim 6, wherein the inspection system comprises at least one of a bright-field inspection system or a dark-field inspection system.

8. The inspection system of claim 6, wherein the illumination system is configured to generate at least one of ultraviolet (UV) light, deep UV light, extreme UV (EUV) light, or vacuum UV light.

9. The inspection system of claim 6, wherein the at least one interposer further comprises:
one or more driver circuitry elements.

10. The inspection system of claim 9, wherein the one or more driver circuitry elements are configured to operate with a voltage swing greater than 4 volts.

11. The inspection system of claim 9, wherein the one or more driver circuitry elements are configured to operate with both negative voltage levels and positive voltage levels.

12. The inspection system of claim 6, wherein the target object comprises:
a semiconductor wafer.

13. An inspection system, comprising:
an illumination source configured to direct illumination toward a surface of a target object disposed on a sample stage;
a detector, the detector comprising at least one light sensing array device, the at least one light sensing array device comprising:
at least one back-thinned light sensing array sensor disposed on at least one interposer, the at least one back-thinned light sensing array sensor further configured for back-illumination, the at least one interposer positioned between the substrate and the at least one light sensing array sensor;
at least two buffer circuits configured to accept outputs of the at least one light sensing array sensor, the at least two buffer circuits being fabricated on the interposer; and
at least two correlated double sampling modules being operatively connected to the interposer and being configured to accept one or more outputs from the at least two buffer circuits, the interposer configured to place each buffer proximate to the output of the at least one light sensing array electrically coupled to the interposer;
a set of focusing optics configured to focus illumination onto the surface of the target object; and
a set of collection optics configured to direct illumination reflected from the surface of the target object to the detector.

14. The inspection system of claim 13, wherein the inspection system comprises at least one of a bright-field inspection system or a dark-field inspection system.

15. The inspection system of claim 13, wherein the illumination system is configured to generate at least one of ultraviolet (UV) light, deep UV light, extreme UV (EUV) light, or vacuum UV light.

16. The inspection system of claim 13 wherein the at least one interposer further comprises:
one or more driver circuitry elements.

17. The inspection system of claim 16, wherein the one or more driver circuitry elements are configured to operate with a voltage swing greater than 4 volts.

18. The inspection system of claim 16, wherein the one or more driver circuitry elements are configured to operate with both negative voltage levels and positive voltage levels.

19. The inspection system of claim 13, wherein the target object comprises:
a semiconductor wafer.

* * * * *